United States Patent
Nakaue et al.

(10) Patent No.: US 11,198,662 B2
(45) Date of Patent: Dec. 14, 2021

(54) FLUOROOLEFIN PRODUCTION METHOD

(71) Applicant: DAIKIN INDUSTRIES, LTD., Osaka (JP)

(72) Inventors: Tsubasa Nakaue, Osaka (JP); Takashi Usui, Osaka (JP); Takehiro Chaki, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 17/044,672

(22) PCT Filed: Apr. 3, 2019

(86) PCT No.: PCT/JP2019/014743
§ 371 (c)(1),
(2) Date: Oct. 1, 2020

(87) PCT Pub. No.: WO2019/194214
PCT Pub. Date: Oct. 10, 2019

(65) Prior Publication Data
US 2021/0070678 A1    Mar. 11, 2021

(30) Foreign Application Priority Data
Apr. 3, 2018 (JP) .............................. JP2018-071488

(51) Int. Cl.
*C07C 17/06* (2006.01)

(52) U.S. Cl.
CPC .......... *C07C 17/06* (2013.01); *C07B 2200/09* (2013.01)

(58) Field of Classification Search
CPC ....... C07C 17/25; C07C 21/18; C07C 17/354; C07C 31/30
See application file for complete search history.

(56) References Cited

U.S. PATENT DOCUMENTS

| 2005/0090698 | A1* | 4/2005 | Merkel | ................. C07C 17/206 |
| | | | | 570/155 |
| 2016/0332938 | A1* | 11/2016 | Nakamura | ............. C09K 5/045 |
| 2018/0162794 | A1 | 6/2018 | Ichinokawa et al. | |
| 2018/0290951 | A1 | 10/2018 | Tomiyori et al. | |

FOREIGN PATENT DOCUMENTS

| JP | 8-104656 | 4/1996 |
| JP | 2007-509942 | 4/2007 |
| JP | 2010-189338 | 9/2010 |
| JP | 2013-237624 | 11/2013 |
| JP | 2016-56132 | 4/2016 |
| WO | 2005/042451 | 5/2005 |
| WO | 2015/115548 | 8/2015 |
| WO | 2017/018412 | 2/2017 |
| WO | 2017/104828 | 6/2017 |
| WO | 2017/104829 | 6/2017 |

OTHER PUBLICATIONS

International Search Report dated May 14, 2019 in International (PCT) Application No. PCT/JP2019/014743.

* cited by examiner

*Primary Examiner* — Jafar F Parsa
(74) *Attorney, Agent, or Firm* — Wenderoth, Lind & Ponack, L.L.P.

(57) ABSTRACT

The present disclosure provides a method for producing fluoroolefin represented by formula (1): $CX^1X^2\!=\!CX^3X^4$, wherein $X^1$, $X^2$, $X^3$, and $X^4$ are the same or different, and represent a hydrogen atom or a fluorine atom, with high selectivity. Specifically, the present disclosure is a method for producing fluoroolefin represented by formula (1), wherein the method includes the step of performing dehydrofluorination by bringing a fluorocarbon represented by formula (2): $CX^1X^2FCX^3X^4H$, wherein $X^1$, $X^2$, $X^3$, and $X^4$ are as defined above, into contact with a base, and the dehydrofluorination step is performed in the liquid phase at a temperature of −70° C. or higher to less than 120° C.

9 Claims, No Drawings

FLUOROOLEFIN PRODUCTION METHOD

TECHNICAL FIELD

The present disclosure relates to a method for producing fluoroolefin.

BACKGROUND ART

Recently, 1,1-difluoroethylene (HFO-1132a) represented by $CF_2=CH_2$, 1,2-difluoroethylene (HFO-1132) represented by $CFH=CFH$, and the like are considered to be promising refrigerant compounds that have a low global warming potential (GWP).

For example, Patent Literature 1 discloses a method for producing HFO-1132a by bringing 1,1,1-trifluoroethane (HFC-143a) or 1,1,2-trifluoroethane (HFC-143) into contact with a metal catalyst such as a metal oxide or metal halide in the presence of water vapor to perform a dehydrofluorination reaction.

Patent Literature 2 discloses a method for producing HFO-1132, comprising the step of subjecting dichlorofluoromethane (HCFC-21) to thermal decomposition in the presence of water vapor to obtain 1,2-dichloro-1,2-difluoroethylene (CFC-1112), and the step of hydrogenating the obtained CFC-1112 in the presence of a hydrogenation catalyst.

Patent Literature 3 discloses a method for producing HFO-1132 by reacting 1-chloro-1,2-difluoroethylene (HCFO-1122a) with hydrogen in the gas phase in the presence of a hydrogenation catalyst.

CITATION LIST

Patent Literature

PTL 1: WO2017/104228
PTL 2: JP2013-237624A
PTL 3: JP2016-056132A

SUMMARY OF INVENTION

Technical Problem

These Patent Literature 1 to 3 do not disclose a method for producing fluoroolefin represented by formula (1): $CX^1X^2=CX^3X^4$, wherein $X^1$, $X^2$, $X^3$, and $X^4$ are the same or different, and represent a hydrogen atom or a fluorine atom, with high selectivity.

An object of the present disclosure is to produce fluoroolefin represented by formula (1) with high selectivity.

Solution to Problem

The present disclosure is as follows.
Item 1. A method for producing a fluoroolefin represented by formula (1): $CX^1X^2=CX^3X^4$, wherein $X^1$, $X^2$, $X^3$, and $X^4$ are the same or different, and represent a hydrogen atom or a fluorine atom,
the method comprising a step of performing dehydrofluorination by bringing a fluorocarbon represented by formula (2) $CX^1X^2FCX^3X^4H$, wherein $X^1$, $X^2$, $X^3$, and $X^4$ are as defined above, into contact with a base,
the dehydrofluorination step being performed in the liquid phase at a temperature of −70° C. or higher to less than 120° C.

Item 2. The production method according to Item 1, wherein the fluoroolefin represented by formula (1) is at least one member selected from the group consisting of 1,2-difluoroethylene (HFO-1132), 1,1-difluoroethylene (HFO-1132a), and trifluoroethylene (HFO-1123).

Item 3. The production method according to Item 1 or 2, wherein the fluorocarbon represented by formula (2) is at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).

Item 4. The production method according to any one of Items 1 to 3, wherein the base is at least one member selected from the group consisting of alkali metal hydroxides, alkali metal carbonates, alkaline earth metal hydroxides, alkaline earth metal carbonates, alkali metal alkoxides, and trialkylamines.

Item 5. The production method according to Item 4, wherein the base is an alkali metal alkoxide.

Item 6. The production method according to Item 5, wherein the alkali metal alkoxide is potassium tert-butoxide (t-BuOK).

Item 7. The production method according to any one of Items 1 to 6, wherein the dehydrofluorination step is performed in an organic solvent.

Item 8. The production method according to Item 7, wherein the organic solvent is at least one member selected from the group consisting of ether compounds, ester compounds, amide compounds, nitrile compounds, and sulfoxide compounds.

Item 9. The production method according to Item 8, wherein the ether compound is at least one member selected from the group consisting of diethyl ether, diisopropyl ether, dibutyl ether, dimethoxyethane, cyclopentyl methyl ether, tert-butyl methyl ether, tetrahydrofuran, 1,4-dioxane, tetrahydropyran, anisole, 1,2-dimethoxyethane, and diethylene glycol dimethyl ether; the ester compound is at least one member selected from the group consisting of methyl acetate, ethyl acetate, propyl acetate, isopropyl acetate, butyl acetate, isobutyl acetate, pentyl acetate, hexyl acetate, methyl propionate, ethyl propionate, propyl propionate, isopropyl propionate, butyl propionate, isobutyl propionate, pentyl propionate, and hexyl propionate; the amide compound is at least one member selected from the group consisting of N-methylformamide, N,N-dimethylformamide, N-methylacetamide, N,N-dimethylacetamide, and N-methylpyrrolidone; the nitrile compound is at least one member selected from the group consisting of acetonitrile, propionitrile, butyronitrile, isobutyronitrile, and benzonitrile; and the sulfoxide compound is at least one member selected from the group consisting of dimethyl sulfoxide, diethyl sulfoxide, dipropyl sulfoxide, diphenyl sulfoxide, and thiophene.

Advantageous Effects of Invention

According to the production method of the present disclosure, fluoroolefin represented by formula (1) above can be produced with high selectivity.

DESCRIPTION OF EMBODIMENTS

As a result of extensive research, the present inventors found that by setting the reaction temperature of the dehydrofluorination reaction when the raw material compound is brought into contact with a base in the liquid phase to perform dehydrofluorination to less than 120° C., high conversion of the raw material compound is achieved, and the fluoroolefin represented by formula (1) is produced with high selectivity.

The present disclosure was completed as a result of further research based on the above findings. The present disclosure includes the following embodiments.

In the method for producing fluoroolefin (sometimes referred to as a "target compound" below) represented by formula (1): $CX^1X^2=CX^3X^4$, wherein $X^1$, $X^2$, $X^3$, and $X^4$ are the same or different, and represent a hydrogen atom or a fluorine atom) comprises the step of performing dehydrofluorination by bringing a fluorocarbon (sometimes referred to as a "raw material compound" below) represented by formula (2): $CX^1X^2FCX^3X^4H$, wherein $X^1$, $X^2$, $X^3$, and $X^4$ are as defined above, into contact with a base.

In the present disclosure, the dehydrofluorination step is performed in the liquid phase at −70° C. or higher to less than 120° C.

In the present disclosure, by satisfying the above requirements, high conversion of the raw material compound is achieved, and the target compound can be obtained with high selectivity.

In the present disclosure, "conversion" refers to the ratio (mol %) of the total molar amount of compounds other than the raw material compound contained in the gas flowing out of the reactor outlet to the molar amount of the raw material compound supplied to the reactor, and "selectivity" refers to the ratio (mol %) of the total molar amount of the target compound contained in the flowing gas to the total molar amount of compounds other than the raw material compound contained in the gas flowing out of the reactor.

Raw Material Compound

In the present disclosure, the raw material compound is a fluorocarbon represented by formula (2): $CX^1X^2FCX^3X^4H$, wherein $X^1$, $X^2$, $X^3$, and $X^4$ are as defined above.

The fluorocarbon represented by formula (2) above is preferably at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a). Of these, 1,1,2-trifluoroethane (HFC-143) is more preferable because the raw material compound is easily available, and production costs and equipment costs can be reduced.

Dehydrofluorination Step

In the dehydrofluorination step in the present disclosure, it is essential to bring the raw material compound into contact with a base in the liquid phase at −70° C. or higher to less than 120° C.

For example, a dehydrofluorination reaction when HFC-134 is used as a raw material compound is performed according to the following reaction formula.

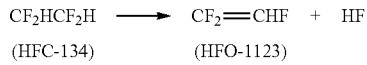

The base is preferably at least one member selected from the group consisting of alkali metal hydroxides, alkali metal carbonates, alkaline earth metal hydroxides, alkaline earth metal carbonates, alkali metal alkoxides, and trialkylamines, because the conversion of the raw material compound is high and the target compound can be obtained with high selectivity. Of these, alkali metal alkoxides are more preferable because the conversion of the raw material compound can be further improved, and the target compound can be obtained with higher selectivity.

As the alkali metal hydroxide, known alkali metal hydroxides can be widely used, and examples thereof include lithium hydroxide, sodium hydroxide, and potassium hydroxide.

As the alkali metal carbonate, well-known alkali metal carbonates can be widely used, and examples thereof include potassium carbonate, sodium carbonate, and cesium carbonate.

As the alkaline earth metal hydroxide, known alkaline earth metal hydroxides can be widely used, and examples thereof include magnesium hydroxide, calcium hydroxide, strontium hydroxide, and barium hydroxide.

As the alkaline earth metal carbonate, known alkaline earth metal carbonates can be widely used, and examples thereof include magnesium carbonate and calcium carbonate.

As the alkali metal alkoxide, known alkali metal alkoxides can be widely used, and examples thereof include lithium methoxide, lithium ethoxide, sodium methoxide, sodium ethoxide, potassium methoxide, potassium ethoxide, and potassium tert-butoxide (t-BuOK). Of these, potassium tert-butoxide (t-BuOK) is particularly preferable because the conversion of the raw material compound can be improved, and the target compound can be obtained with high selectivity.

As the trialkylamine, known trialkylamines can be widely used, and examples thereof include trimethylamine, triethylamine, tripropylamine, tributylamine, and trioctylamine.

The amount of the base is usually 1 to 6 moles, preferably 1.2 to 4 moles, more preferably 1.4 to 3 moles, still more preferably 1.5 to 2.5 moles, relative to 1 mole of the raw material compound. When the amount of the base is within such a range, the conversion of the raw material compound can be improved, and the target compound can be obtained with high selectivity.

The reaction temperature of the dehydrofluorination reaction is −70° C. or higher to less than 120° C. When the reaction temperature is less than −70° C. or 120° C. or higher, the conversion of the raw material compound and the selectivity of the target compound may be reduced due to the decrease in the selectivity of dehydrogen fluoride.

The reaction temperature is preferably −70 to 100° C., more preferably −40 to 30° C., even more preferably −30 to 10° C., and particularly preferably −20 to 0° C., from the viewpoint of improving the reaction rate of the dehydrofluorination reaction.

The dehydrofluorination reaction is preferably carried out in an organic solvent because the conversion of the raw material compound is high, and the target compound can be obtained with high selectivity.

The organic solvent is preferably at least one member selected from the group consisting of ether compounds, ester compounds, amide compounds, nitrile compounds, and sulfoxide compounds.

The ether compound is preferably at least one member selected from the group consisting of diethyl ether, diisopropyl ether, dibutyl ether, dimethoxyethane (DME), cyclopentyl methyl ether (CPME), tert-butyl methyl ether, tetrahydrofuran (THF), 1,4-dioxane, tetrahydropyran, anisole, 1,2-dimethoxyethane, and diethylene glycol dimethyl ether. Among these ether compounds, tetrahydrofuran (THF) is particularly preferable because the conversion of the raw material compound is further increased, and the target compound can be obtained with higher selectivity.

The ester compound is at least one member selected from the group consisting of methyl acetate, ethyl acetate, propyl acetate, isopropyl acetate, butyl acetate, isobutyl acetate, pentyl acetate, hexyl acetate, methyl propionate, ethyl propionate, propyl propionate, isopropyl propionate, butyl propionate, isobutyl propionate, pentyl propionate, and hexyl propionate. Among these ester compounds, ethyl acetate is particularly preferable because the conversion of the raw material compound is further increased, and the target compound can be obtained with higher selectivity.

The amide compound is at least one member selected from the group consisting of N-methylformamide, N,N-dimethylformamide (DMF), N-methylacetamide, N,N-dimethylacetamide (DMA), and N-methylpyrrolidone (NMP). Among these amide compounds, N,N-dimethylformamide (DMF) is particularly preferable because the conversion of the raw material compound is further increased, and the target compound can be obtained with higher selectivity.

The nitrile compound is preferably at least one member selected from the group consisting of acetonitrile (ACN), propionitrile, butyronitrile, isobutyronitrile, and benzonitrile. Among these nitrile compounds, acetonitrile (ACN) is particularly preferable because the conversion of the raw material compound is further increased, and the target compound can be obtained with higher selectivity.

The sulfoxide compound is preferably at least one member selected from the group consisting of dimethyl sulfoxide (DMSO), diethyl sulfoxide, dipropyl sulfoxide, diphenyl sulfoxide, and thiophene. Among these sulfoxide compounds, dimethyl sulfoxide (DMSO) is particularly preferable because the conversion of the raw material compound is further increased, and the target compound can be obtained with higher selectivity.

From the viewpoint of more efficiently advancing the dehydrofluorination reaction, the reaction pressure in the dehydrofluorination reaction is preferably 0.1 to 1.5 MPa, more preferably 0.15 to 1.25 MPa, and even more preferably 0.2 to 1 MPa.

The dehydrofluorination reaction can be performed either in batch mode or in flow mode in which a raw material compound is continuously fed to a reactor and the target compound is continuously withdrawn from the reactor. When the target compound stays in the reactor, the dehydrofluorination reaction can further proceed. In view of this, the dehydrofluorination reaction is preferably performed in flow mode.

Target Compound

The target compound in the present disclosure is fluoroolefin represented by formula (1): $CX^1X^2=CX^3X^4$, wherein $X^1$, $X^2$, $X^3$, and $X^4$ are the same or different, and represent a hydrogen atom or a fluorine atom.

The fluoroolefin represented by formula (1) is at least one member selected from the group consisting of 1,2-difluoroethylene (HFO-1132), 1,1-difluoroethylene (HFO-1132a), and trifluoroethylene (HFO-1123). Of these, HFO-1132 is more preferable.

EXAMPLES

The present disclosure will be specifically described below with reference to Examples. However, the present disclosure is not limited to these Examples.

Example 1 tBuOK (13 g, 0.11 mol) as a base and DMF (30 mL) as an organic solvent were added to a 50-mL reactor. The reactor was immersed in an ice bath, and cooled to an internal temperature of 0° C. HFC-143 (4.65 g, 0.05 mol) was added as a raw material compound to the reactor. The pressure in the reactor was set to 0.2 MPa to perform a dehydrofluorination reaction. The dehydrofluorination reaction was completed in 3 hours. After completion of the reaction, mass spectrometry was performed according to the gas chromatography/mass spectrometry (GC/MS) method, and structural analysis according to NMR spectroscopy was performed. The results of the mass spectrometry and structural analysis confirmed the generation of (E)-HFO-1132 and (Z)-HFO-1132. The conversion of HFC-143 was 97 mol %. The total yield (selectivity) of (E)-HFO-1132 and (Z)-HFO-1132 was 86 mol %.

Example 2 tBuOK (266.2 g, 2.37 mol) as a base and DMF (500 mL) as an organic solvent were added to a 1000-mL reactor. The reactor was immersed in an ice bath, and cooled to an internal temperature of 0° C. HFC-143 (185.9 g, 2.21 mol) was added as a raw material compound to the reactor. The pressure in the reactor was set to 0.2 MPa to perform a dehydrofluorination reaction. The dehydrofluorination reaction was completed in 3 hours. After completion of the reaction, mass spectrometry was performed according to the gas chromatography/mass spectrometry (GC/MS) method, and structural analysis according to NMR spectroscopy was performed. The results of the mass spectrometry and structural analysis confirmed the generation of (E)-HFO-1132 and (Z)-HFO-1132. The conversion of HFC-143 was 100 mol %. The total yield (selectivity) of (E)-HFO-1132 and (Z)-HFO-1132 was 93 mol %.

Example 3

The same treatment as in Example 1 was performed, except that DMSO was used as an organic solvent in place of DMF, thus obtaining (E)-HFO-1132 and (Z)-HFO-1132. The conversion of HFC-143 was 90 mol %. The total yield (selectivity) of (E)-HFO-1132 and (Z)-HFO-1132 was 85 mol %.

The invention claimed is:
1. A method for producing a fluoroolefin represented by formula (1): $CX^1X^2=CX^3X^4$, wherein $X^1$, $X^2$, $X^3$, and $X^4$ are the same or different, and represent a hydrogen atom or a fluorine atom, and wherein at least one of $X^1$, $X^2$, $X^3$, and $X^4$ represents a fluorine atom,
the method comprising a step of performing dehydrofluorination by bringing a fluorocarbon represented by formula (2): $CX^1X^2FCX^3X^4H$, wherein $X^1$, $X^2$, $X^3$, and $X^4$ are the same or different, and represent a hydrogen atom or a fluorine atom, into contact with a base,
the dehydrofluorination step being performed in the liquid phase at a temperature of −70° C. or higher to 0° C. or less.
2. The production method according to claim 1, wherein the fluoroolefin represented by formula (1) is at least one member selected from the group consisting of 1,2-difluoroethylene (HFO-1132), 1,1-difluoroethylene (HFO-1132a), and trifluoroethylene (HFO-1123).

3. The production method according to claim 1, wherein the fluorocarbon represented by formula (2) is at least one member selected from the group consisting of 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).

4. The production method according to claim 1, wherein the base is at least one member selected from the group consisting of alkali metal hydroxides, alkali metal carbonates, alkaline earth metal hydroxides, alkaline earth metal carbonates, alkali metal alkoxides, and trialkylamines.

5. The production method according to claim 4, wherein the base is an alkali metal alkoxide.

6. The production method according to claim 5, wherein the alkali metal alkoxide is potassium tert-butoxide (t-BuOK).

7. The production method according to claim 1, wherein the dehydrofluorination step is performed in an organic solvent.

8. The production method according to claim 7, wherein the organic solvent is at least one member selected from the group consisting of ether compounds, ester compounds, amide compounds, nitrile compounds, and sulfoxide compounds.

9. The production method according to claim 8, wherein the ether compound is at least one member selected from the group consisting of diethyl ether, diisopropyl ether, dibutyl ether, dimethoxyethane, cyclopentyl methyl ether, tert-butyl methyl ether, tetrahydrofuran, 1,4-dioxane, tetrahydropyran, anisole, 1,2-dimethoxyethane, and diethylene glycol dimethyl ether; the ester compound is at least one member selected from the group consisting of methyl acetate, ethyl acetate, propyl acetate, isopropyl acetate, butyl acetate, isobutyl acetate, pentyl acetate, hexyl acetate, methyl propionate, ethyl propionate, propyl propionate, isopropyl propionate, butyl propionate, isobutyl propionate, pentyl propionate, and hexyl propionate; the amide compound is at least one member selected from the group consisting of N-methylformamide, N,N-dimethylformamide, N-methylacetamide, N,N-dimethylacetamide, and N-methylpyrrolidone; the nitrile compound is at least one member selected from the group consisting of acetonitrile, propionitrile, butyronitrile, isobutyronitrile, and benzonitrile; and the sulfoxide compound is at least one member selected from the group consisting of dimethyl sulfoxide, diethyl sulfoxide, dipropyl sulfoxide, diphenyl sulfoxide, and thiophene.

* * * * *